United States Patent
Namiki et al.

(10) Patent No.: US 6,329,382 B1
(45) Date of Patent: Dec. 11, 2001

(54) PYRROLO[3,2-E]PYRAZOLO[1,5-A] PYRIMIDINE REMEDIES/PREVENTIVES FOR RESPIRATORY DISEASES

(75) Inventors: Takayuki Namiki; Masayuki Yuasa; Takako Takakuwa; Satoshi Ichinomiya; Masashi Tamai; Naoki Hiyama; Yukio Kawazu; Tomoaki Yahiro; Mayumi Sugio, all of Yokohama (JP)

(73) Assignee: Pola Chemical Industries, Inc., Shizuoka (JP)

( * ) Notice: Subject to any disclaimer, the term of this patent is extended or adjusted under 35 U.S.C. 154(b) by 0 days.

(21) Appl. No.: 09/355,935

(22) PCT Filed: Dec. 26, 1997

(86) PCT No.: PCT/JP97/04878

§ 371 Date: Aug. 13, 1999

§ 102(e) Date: Aug. 13, 1999

(87) PCT Pub. No.: WO98/35968

PCT Pub. Date: Aug. 20, 1998

(51) Int. Cl.[7] .................... C07D 487/14; A61K 31/519; A61P 11/06; A61P 11/08
(52) U.S. Cl. ............................ 514/267; 544/251
(58) Field of Search ............... 544/251; 514/267

(56) References Cited

U.S. PATENT DOCUMENTS 4,992,442 * 2/1991 Tsujitani et al. ............. 514/267

FOREIGN PATENT DOCUMENTS 7-242670 * 9/1995 (JP) .
7-267960 * 10/1995 (JP) .
98 33799  8/1998 (WO) .

\* cited by examiner

Primary Examiner—Mukund J. Shah
Assistant Examiner—Thomas McKenzie
(74) Attorney, Agent, or Firm—Oblon, Spivak, McClelland, Maier & Neustadt, P.C.

(57) ABSTRACT

The invention relates to a therapeutic and preventive medicament for respiratory diseases, comprising, as an active ingredient, a compound represented by the general formula (1):

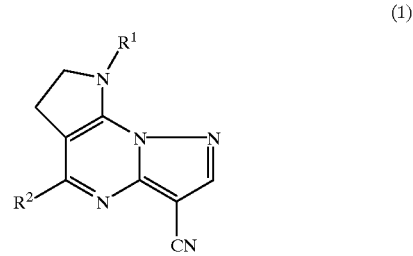

(1)

wherein $R^1$ represents a linear, branched or cyclic alkyl group having 1 to 10 carbon atoms; and $R^2$ represents a hydrogen or halogen atom, a substituted alkyl group, an amino group which may be substituted, a carboxyl group, an alkoxycarbonyl group, a carbamoyl group, or an alkylcarbamoyl group, or a salt thereof. This compound has excellent tracheobronchodilative effect and inhibitory effect on airway constriction.

8 Claims, No Drawings

PYRROLO[3,2-E]PYRAZOLO[1,5-A] PYRIMIDINE REMEDIES/PREVENTIVES FOR RESPIRATORY DISEASES

This application is the National Stage Application of PCT/JP 97/04878, filed Dec. 26, 1997, which claims priority to Japanese Applications 9-047197 and 9-047211 filed Feb. 14, 1997.

TECHNICAL FIELD

The present invention relates to a therapeutic and preventive medicament for respiratory diseases represented by asthma in particular, and to novel pyrrolopyrazolopyrimidine derivatives.

BACKGROUND ART

At present, bronchodilation by xanthine type bronchodilators typified by theophylline are mainly practiced for the prevention and treatment of respiratory diseases represented by asthma and the like. Besides, beta-receptor stimuli such as ephedrine hydrochloride have been only used symptomatolytically.

However, all the above drugs have great side effects and hence have offered a problem. However, there has been nothing for it but to administer these drugs because any excellent drug substitutable for these drugs has not been yet found.

On the other hand, 3-cyano-5-methylpyrrolo[3,2-e]pyrazolo[1,5-a]pyrimidines as compounds having a pyrrolo[3,2-e]pyrazolo[1,5-a]pyrimidine skeleton have been known to have excellent vasodilative effect and tracheobronchodilative effect (Japanese Patent Publication No. 88999/1994). However, these compounds have been difficult to separate their action on circulatory organs such as hypotensive effect and their action on tracheas (or bronchus) from each other. It has therefore been desired to develop a drug which selectively acts on tracheas (or bronchus).

It is therefore an object of the present invention to provide a medicine which scarcely exhibits side effects and has excellent prophylactic and therapeutic effects on respiratory diseases.

DISCLOSURE OF THE INVENTION

In view of the foregoing circumstances, the present inventors have carried out an extensive investigation by syntheses, screening and the like with a view toward seeking compounds useful in the prevention and treatment of respiratory diseases. As a result, it has been found that compounds represented by the general formula (1), which will be described subsequently, or salts thereof have excellent tracheobronchodilative effect and inhibitory effect on airway constriction, act only weakly on circulatory organs, and are hence useful as prophylactic and therapeutic medicines for respiratory diseases, thus leading to completion of the present invention.

According to the present invention, there is thus provided a therapeutic and preventive medicament for respiratory diseases, comprising, as an active ingredient, a pyrrolopyrazolo-pyrimidine derivative represented by the following general formula (1):

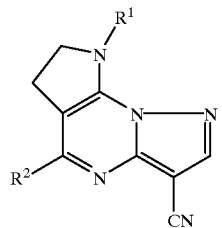

(1)

wherein $R^1$ represents a linear, branched or cyclic alkyl group having 1 to 10 carbon atoms; and $R^2$ represents a hydrogen or halogen atom, a substituted alkyl group, an amino group which may be substituted, a carboxyl group, an alkoxycarbonyl group, a carbamoyl group, or an alkylcarbamoyl group, or a salt thereof.

According to the present invention, there is also provided a therpeutic and preventive medicament composition for respiratory diseases, comprising a compound represented by the general formula (1) or a salt thereof and a pharmaceutically acceptable carrier.

According to the present invention, there is further provided use of a compound represented by the general formula (1) or a salt thereof for a therapeutic and preventive medicament for respiratory diseases.

According to the present invention, there is still further provided a method for the treatment of a respiratory disease, which comprises the administration of an effective amount of a compound represented by the general formula (1) or a salt thereof.

Of the compounds represented by the general formula (1), compounds represented by the general formula (1A), which will be described subsequently, are novel compounds not found in literature.

According to the present invention, therefore, there are yet still further provided a pyrrolopyrazolopyrimidine derivative represented by the following general formula (1A):

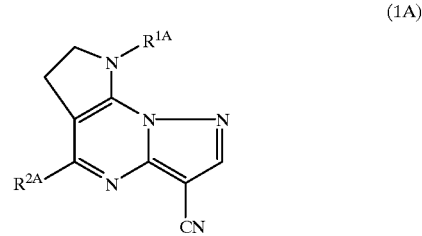

(1A)

wherein $R^{1A}$ represents a linear, branched or cyclic alkyl group having 1 to 10 carbon atoms (but a tert-butyl group); and $R^{2A}$ represents a halogen atom, a substituted alkyl group, an amino group which may be substituted, a carboxyl group, an alkoxycarbonyl group, a carbamoyl group, or an alkylcarbamoyl group, or a salt thereof.

BEST MODE FOR CARRYING OUT THE INVENTION

In the general formula (1), $R^1$ is a linear, branched or cyclic alkyl group having 1 to 10 carbon atoms. $R^{1A}$ is any one of those represented by $R^1$ but a tert-butyl group. Specific examples of $R^1$ include methyl, ethyl, n-propyl, isopropyl, cyclopropyl, n-butyl, isobutyl, sec-butyl, tert-butyl, cyclobutyl, n-pentyl, isopentyl, 1-ethylpropyl, tert-amyl, cyclopentyl, n-hexyl, cyclohexyl, n-heptyl and cycloheptyl groups. Of these, isopropyl, cyclopropyl, sec-butyl, tert-butyl, cyclobutyl, 1-ethylpropyl, tert-amyl, cyclopentyl and cyclohexyl groups are preferred as $R^1$. Preferable examples of $R^{1A}$ include these groups other than the tert-butyl group.

Examples of the halogen atoms represented by $R^2$ and $R^{2A}$ include fluorine, chlorine and bromine atoms. Of these, fluorine and chlorine atoms are preferred.

Examples of the substituted alkyl group include alkoxyalkyl groups, aryloxyalkyl groups, aralkyloxyalkyl groups, mono- or di-alkyl-aminoalkyl groups, cyclic aminoalkyl groups, and hydroxyalkyl groups. Of these, $C_{1-10}$-alkoxy-$C_{1-10}$-alkyl groups, phenoxy-$C_{1-10}$-alkyl groups, phenyl-$C_{1-4}$-alkyloxy-$C_{1-10}$-alkyl groups, mono- or di-$C_{1-10}$-alkylamino-$C_{1-10}$-alkyl groups, cyclic amino-$C_{1-10}$-alkyl groups and hydroxy-$C_{1-10}$-alkyl groups are preferred. Specific examples thereof include methoxymethyl, ethoxymethyl, benzyloxymethyl, phenoxymethyl, aminomethyl, methylaminomethyl, dimethylaminomethyl, morpholinomethyl, piperazinomethyl, 4-methylpiperazinomethyl and hydroxymethyl groups.

Examples of the amino group which may be substituted include an amino group, mono- or di-alkylamino groups, cyclic amino groups, alkylsulfonylamino groups which may be substituted by halogen atoms, arylsulfonylamino groups, alkylcarbonylamino groups, arylcarbonylamino groups, a ureido group which may be substituted, a thioureido group which may be substituted, and a hydrazino group which may be substituted. The halogen atoms as substituents include fluorine, chlorine, bromine and iodine atoms. Examples of the substituents on the ureido, thioureido and hydrazino groups include linear, branched or cyclic alkyl groups. Of these alkyl groups, those having 1 to 10 carbon atoms are preferred. Preferable examples of the amino groups which may be substituted include an amino group, mono- or di-$C_{1-10}$-alkylamino groups, three- to six-membered cyclic amino groups, $C_{1-10}$-alkylsulfonylamino groups, $C_{1-10}$-halogenoalkylsulfonylamino groups, a benzenesulfonylamino group, $C_{1-10}$-alkylcarbonylamino groups, $C_{6-10}$-arylcarbonylamino groups, $C_{1-10}$-alkylureido groups, $C_{1-10}$-alkylthioureido groups, and $C_{1-10}$-alkylhydrazino groups. Specific examples of the amino group which may be substituted include amino, methylamino, ethylamino, dimethylamino, diethylamino, cyclopropylamino, cyclobutylamino, pyrrolidino, piperidino, morpholino, piperazino, methanesulfonylamino, trifluoromethanesulfonylamino, benzenesulfonylamino, acetylamino, benzoylamino, ureido, methylureido, thioureido, methylthioureido, hydrazino and methylhydrazino groups.

The alkoxycarbonyl group is preferably an alkoxycarbonyl group having 2 to 11 carbon atoms in total, and more preferably an alkoxycarbonyl group having 2 to 7 carbon atoms in total. Examples of the alkoxycarbonyl group include methoxycarbonyl, ethoxycarbonyl and isopropyloxycarbonyl groups.

The alkylcarbamoyl group is preferably an alkylcarbamoyl group having 2 to 11 carbon atoms in total, and more preferably an alkylcarbamoyl group having 2 to 7 carbon atoms in total. Examples of the alkylcarbamoyl group include methylcarbamoyl, ethylcarbamoyl, isopropylcarbamoyl, dimethylcarbamoyl and diethylcarbamoyl groups.

Of these groups, an amino group, halogen atom (particularly, a chlorine atom) or a hydrogen atom is preferred as $R^2$, while an amino group or halogen atom (particularly, a chlorine atom) is preferred as $R^{2A}$.

As specific examples of the compound (1), may be mentioned:

3-cyano-8-cyclopentyl-6,7-dihydro-8H-pyrrolo[3,2-e]pyrazolo[1,5-a]pyrimidine (Compound 1), 8-sec-butyl-3-cyano-6,7-dihydro-8H-pyrrolo[3,2-e]pyrazolo[1,5-a]pyrimidine (Compound 2), 3-cyano-6,7-dihydro-8-isopropyl-8H-pyrrolo[3,2-e]pyrazolo[1,5-a]-pyrimidine, 3-cyano-8-cyclopropyl-6,7-dihydro-8H-pyrrolo[3,2-e]pyrazolo[1,5-a]pyrimidine, 3-cyano-8-cyclobutyl-6,7-dihydro-8H-pyrrolo[3,2-e]pyrazolo[1,5-a]pyrimidine, 3-cyano-6,7-dihydro-8-(1-ethylpropyl)-8H-pyrrolo[3,2-e]pyrazolo[1,5-a]pyrimidine, 3-cyano-8-cyclohexyl-6,7-dihydro-8H-pyrrolo[3,2-e]pyrazolo[1,5-a]pyrimidine, 5-chloro-3-cyano-8-cyclopentyl-6,7-dihydro-8H-pyrrolo[3,2-e]pyrazolo[1,5-a]pyrimidine (Compound 3), 8-sec-butyl-5-chloro-3-cyano-6,7-dihydro-8H-pyrrolo[3,2-e]pyrazolo[1,5-a]pyrimidine (Compound 4), 5-chloro-3-cyano-6,7-dihydro-8-isopropyl-8H-pyrrolo[3,2-e]pyrazolo[1,5-a]pyrimidine, 5-chloro-3-cyano-8-cyclopropyl-6,7-dihydro-8H-pyrrolo[3,2-e]pyrazolo[1,5-a]pyrimidine, 5-chloro-3-cyano-8-cyclobutyl-6,7-dihydro-8H-pyrrolo[3,2-e]pyrazolo[1,5-a]pyrimidine, 5-chloro-3-cyano-6,7-dihydro-8-(1-ethylpropyl)-8H-pyrrolo[3,2-e]pyrazolo[1,5-a]pyrimidine, 5-chloro-3-cyano-8-cyclohexyl-6,7-dihydro-8H-pyrrolo[3,2-e]pyrazolo[1,5-a]pyrimidine, 5-amino-3-cyano-8-cyclopentyl-6,7-dihydro-8H-pyrrolo[3,2-e]pyrazolo[1,5-a]pyrimidine (Compound 5), 5-amino-3-cyano-8-cyclohexyl-6,7-dihydro-8H-pyrrolo[3,2-e]pyrazolo[1,5-a]pyrimidine (Compound 6), 5-amino-8-sec-butyl-3-cyano-6,7-dihydro-8H-pyrrolo[3,2-e]pyrazolo[1,5-a]pyrimidine (Compound 7), 5-amino-3-cyano-6,7-dihydro-8-isopropyl-8H-pyrrolo[3,2-e]pyrazolo[1,5-a]pyrimidine, 5-amino-3-cyano-8-cyclopropyl-6,7-dihydro-8H-pyrrolo[3,2-e]pyrazolo[1,5-a]pyrimidine, 5-amino-3-cyano-8-cyclobutyl-6,7-dihydro- 8H-pyrrolo[3,2-e]pyrazolo[1,5-a]-pyrimidine, 5-amino-3-cyano-6,7-dihydro-8-(1-ethylpropyl)-8H-pyrrolo[3,2-e]pyrazolo[1,5-a]pyrimidine, 3-cyano-8-cyclopentyl-6,7-dihydro-8H-pyrrolo[3,2-e]pyrazolo[1,5-a]pyrimidine-5-carboxylic acid (Compound 8), 3-cyano-8-cyclohexyl-6,7-dihydro-8H-pyrrolo[3,2-e]pyrazolo[1,5-a]pyrimidine-5-carboxylic acid (Compound 9), 8-sec-butyl-3-cyano-6,7-dihydro-8H-pyrrolo[3,2-e]pyrazolo[1,5-a]pyrimidine-5-carboxylic acid (Compound 10), 3-cyano-6,7-dihydro-8-isopropyl-8H-pyrrolo[3,2-e]pyrazolo[1,5-a]pyrimidine-5-carboxylic acid, 3-cyano-8-cyclopropyl-6,7-dihydro-8H-pyrrolo[3,2-e]pyrazolo[1,5-a]pyrimidine-5-carboxylic acid, 3-cyano-8-cyclobutyl-6,7-dihydro-8H-pyrrolo[3,2-e]pyrazolo[1,5-a]pyrimidine-5-carboxylic acid, 3-cyano-6,7-dihydro-8-(1-ethylpropyl)-8H-pyrrolo[3,2-e]pyrazolo[1,5-a]-pyrimidine-5-carboxylic acid, ethyl 3-cyano-8-cyclopentyl-6,7-dihydro-8H-pyrrolo[3,2-e]pyrazolo[1,5-a]pyrimidine-5-carboxylate (Compound 11), ethyl 3-cyano-8-cyclohexyl-6,7-dihydro-8H-pyrrolo[3,2-e]pyrazolo[1,5-a]pyrimidine-5-carboxylate (Compound 12), ethyl 8-sec-butyl-3-cyano-6,7-dihydro-8H-pyrrolo[3,2-e]pyrazolo[1,5-a]pyrimidine-5-carboxylate (Compound 13), ethyl 3-cyano-6,7-dihydro-8-isopropyl- 8H-pyrrolo[3,2-e]pyrazolo[1,5-a]pyrimidine-5-carboxylate, ethyl 3-cyano-8-cyclopropyl-6,7-dihydro-8H-pyrrolo[3,2-e]pyrazolo[1,5-a]pyrimidine-5-carboxylate, ethyl 3-cyano-8-cyclobutyl-6,7-dihydro-8H-pyrrolo[3,2-e]pyrazolo[1,5-a]pyrimidine-5-carboxylate, ethyl 3-cyano-6,7-dihydro-8-(1-ethylpropyl)-8H-pyrrolo[3,2-e]pyrazolo[1,5-a]pyrimidine-5-carboxylate, 8-tert-butyl-3-cyano-6,7-dihydro-8H-pyrrolo[3,2-e]pyrazolo[1,5-a]pyrimidine (Compound 14), 8-tert-butyl-5-chloro-3-cyano-6,7-dihydro-8H-pyrrolo[3,2-e]pyrazolo[1,5-a]pyrimidine (Compound 15), 5-amino-8-tert-butyl-3-cyano-6,7-dihydro-8H-pyrrolo[3,2-e]pyrazolo[1,5-a]pyrimidine (Compound 16), 8-tert-butyl-3-cyano-6,7-dihydro-8H-pyrrolo[3,2-e]pyrazolo[1,5-a]pyrimidine-5-carboxylic acid (Compound 17), ethyl 8-tert-butyl-3-cyano-6,7-dihydro-8H-pyrrolo[3,2-e]pyrazolo[1,5-a]pyrimidine-5-carboxylate (Compound 18), 8-sec-butyl-3-cyano-6,7-dihydro-5-methoxymethyl-8H-pyrrolo[3,2-e]pyrazolo[1,5-a]pyrimidine, 8-sec-butyl-3-cyano-6,7-dihydro-5-ethoxymethyl-8H-pyrrolo[3,2-e]pyrazolo[1,5-a]pyrimidine, 5-benzyloxymethyl-8-sec-butyl-3-cyano-6,7-dihydro8H-pyrrolo[3,2-e]pyrazolo[1,5-a]pyrimidine, 8-sec-butyl-3-cyano-6,7-dihydro-5-phenoxymethyl-8H-pyrrolo[3,2-e]pyrazolo[1,5-a]pyrimidine, 5-aminomethyl-8-sec-butyl-3-cyano-6,7-dihydro-8H-pyrrolo[3,2-e]pyrazolo-[1,5-a]pyrimidine, 8-sec-butyl-3-cyano-6,7-dihydro-5-methylaminomethyl-8H-pyrrolo[3,2-e]pyrazolo[1,5-a]pyrimidine, 8-sec-butyl-3-cyano-6,7-dihydro-5-dimethylaminomethyl-8H-pyrrolo[3,2-e]pyrazolo[1,5-a]pyrimidine, 8-sec-butyl-3-cyano-6,7-dihydro-5-morpholinomethyl-8H-pyrrolo[3,2-e]pyrazolo[1,5-a]pyrimidine, 8-sec-butyl-3-cyano-6,7-dihydro-5-piperazinomethyl-8H-pyrrolo[3,2-e]pyrazolo[1,5-a]pyrimidine, 8-sec-butyl-3-cyano-6,7-dihydro-5-(4-methyl-piperazinomethyl)-8H-pyrrolo[3,2-e]pyrazolo[1,5-a]pyrimidine, 8-sec-butyl-3-cyano-6,7-dihydro-5-hydroxymethyl-8H-pyrrolo[3, 2-e]pyrazolo[1, 5-a]pyrimidine, 8-sec-butyl-3-cyano-6,7-dihydro-5-methylamino-8H-pyrrolo[3,2-e]pyrazolo[1,5-a]pyrimidine, 8-sec-butyl-3-cyano-6,7-dihydro-5-ethylamino-8H-pyrrolo[3,2-e]pyrazolo[1,5-a]pyrimidine, 8-sec-butyl-3-cyano-6,7-dihydro-5-dimethylamino-8H-pyrrolo[3,2-e]pyrazolo[1,5-a]pyrimidine, 8-sec-butyl-3-cyano-5-diethylamino-6,7-dihydro-8H-pyrrolo[3,2-e]pyrazolo[1,5-a]pyrimidine, 8-sec-butyl-3-cyano-5-cyclopropylamino-6,7-dihydro-8H-pyrrolo[3,2-e]pyrazolo[1,5-a]pyrimidine, 8-sec-butyl-3-cyano-5-cyclobutylamino-6,7-dihydro-8H-pyrrolo[3,2-e]pyrazolo[1,5-a]pyrimidine, 8-sec-butyl-3-cyano-6,7-dihydro-5-pyrrolidino-8H-pyrrolo[3,2-e]pyrazolo[1,5-a]pyrimidine, 8-sec-butyl-3-cyano-6,7-dihydro-5-piperidino-8H-pyrrolo[3,2-e]pyrazolo[1,5-a]pyrimidine, 8-sec-butyl-3-cyano-6,7-dihydro-5-morpholino-8H-pyrrolo[3,2-e]pyrazolo[1,5-a]pyrimidine, 8-sec-butyl-3-cyano-6,7-dihydro-5-piperazino-8H-pyrrolo[3,2-e]pyrazolo[1,5-a]pyrimidine, 8-sec-butyl-3-cyano-6,7-dihydro-5-methanesulfonylamino-8H-pyrrolo[3,2-e]pyrazolo[1,5-a]pyrimidine, 8-sec-butyl-3-cyano-6,7-dihydro-5-trifluoromethanesulfonylamino-8H-pyrrolo[3,2-e]pyrazolo[1,5-a]pyrimidine, 5-benzenesulfonylamino-8-sec-butyl-3-cyano-6,7-dihydro-8H-pyrrolo[3,2-e]pyrazolo[1,5-a]pyrimidine, 5-acetylamino-8-sec-butyl-3-cyano-6,7-dihydro-8H-pyrrolo[3,2-e]pyrazolo[1,5-a]pyrimidine, 5-benzoylamino-8-sec-butyl-3-cyano-6,7-dihydro-8H-pyrrolo[3,2-e]pyrazolo[1,5-a]pyrimidine, 8-sec-butyl-3-cyano-6,7-dihydro-5-ureido-8H-pyrrolo[3,2-e]pyrazolo[1,5-a]pyrimidine, 8-sec-butyl-3-cyano-6,7-dihydro-5-methylureido-8H-pyrrolo[3,2-e]pyrazolo[1,5-a]pyrimidine, 8-sec-butyl-3-cyano-6,7-dihydro-5-thioureido-8H-pyrrolo[3,2-e]pyrazolo[1,5-a]pyrimidine, 8-sec-butyl-3-cyano-6,7-dihydro-5-methylthioureido-8H-pyrrolo[3,2-e]pyrazolo[1,5-a]pyrimidine, 8-sec-butyl-3-cyano-6,7-dihydro-5-hydrazino-8H-pyrrolo[3,2-e]pyrazolo[1,5-a]pyrimidine, and 8-sec-butyl-3-cyano-6,7-dihydro-5-methylhydrazino-8H-pyrrolo[3,2-e]pyrazolo[1,5-a]pyrimidine.

No particular limitation is imposed on the salts usable in the present invention so far as they are physiologically acceptable salts. However, preferable examples of the salts include mineral acid salts such as hydrochlorides, sulfates, nitrates and phosphates; organic acid salts such as citrates, oxalates, fumarates, maleates, formates, acetates, tartrates, methanesulfonates, benzenesulfonates and p-toluenesulfonates; and carbonates.

The compounds (1) also include solvates thereof such as hydrates.

A compound in which $R^2$ in the general formula (1) is an amino group which may be substituted, or an alkoxycarbonyl group can be prepared in accordance with, for example, the following reaction scheme:

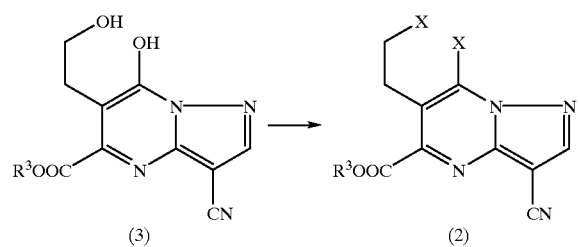

-continued

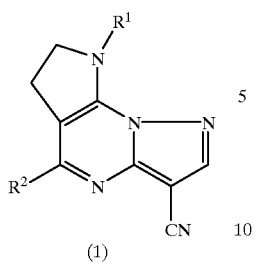

(1)

wherein $R^1$ and $R^2$ have the same meanings as defined above, $R^3$ represents an alkyl group, and X represents a halogen atom.

A compound (3), in which an alkoxycarbonyl group has been introduced in advance, or a tautomer thereof is first allowed to react with a halogenating agent such as phosphoryl chloride to convert it into a dihalogenated product (2). An amine ($H_2N$—$R^1$) is then allowed to act on the dihalogenated product to cyclize it, thereby giving a compound (1) in which $R^2$ is an alkoxycarbonyl group. The alkoxycarbonyl group of this compound is then hydrolyzed, thereby giving a compound (1) in which $R^2$ is a carboxyl group. Further, the compound (1) in which $R^2$ is a carboxyl group is aminated utilizing a Curtius rearrangement reaction, and a substituent is introduced into the amino group of the resultant aminated product in accordance with a method known per se in the art if desired, whereby a compound (1), in which $R^2$ is an amino group which may be substituted, can be obtained.

Here, the tautomer of the compound (3) includes that having the following structure:

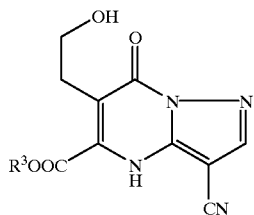

The compound (3) used herein can be prepared in accordance with the following process (a): Process (a):

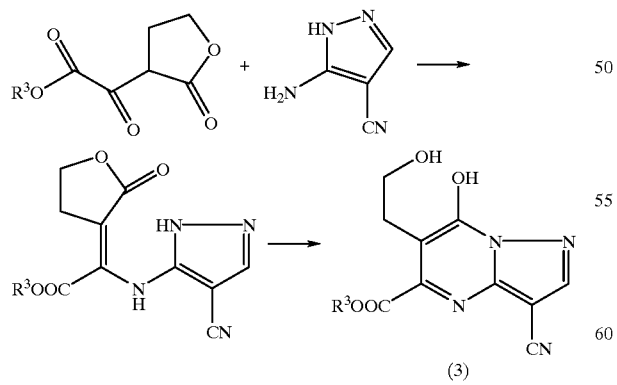

(3)

wherein $R^3$ represents an alkyl group.

More specifically, 3-amino-4-cyanopyrazol and an alkyl (tetrahydro-2-oxo-3-furyl) glyoxylate are condensed using a Lewis acid or the like as a catalyst, and a formed product is then cyclized by the treatment with an alkali, whereby the compound (3) or the tautomer thereof can be obtained.

The alkyl (tetrahydro-2-oxo-3-furyl) glyoxylate is obtained by the treatment of γ-butyrolactone with an oxalic diester in the presence of an alkali catalyst.

A compound in which $R^2$ in the general formula (1) is a hydrogen or halogen atom can be prepared in accordance with, for example, the following reaction scheme:

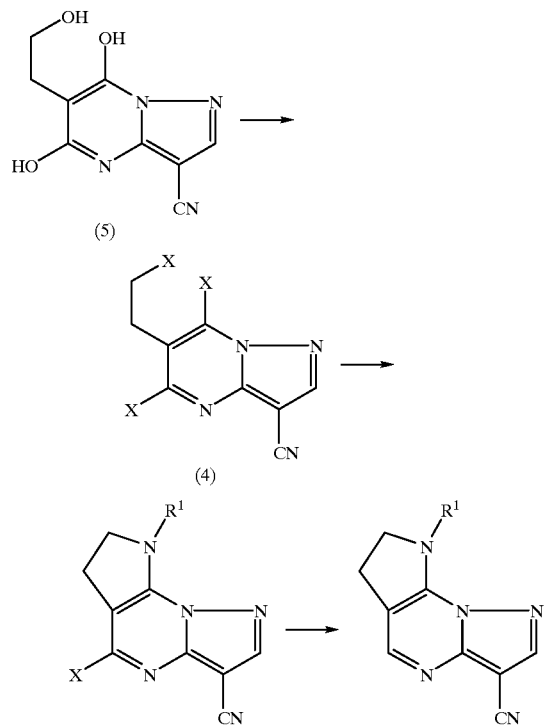

wherein $R^1$ has the same meaning as defined above, and X represents a halogen atom.

More specifically, a halogenating agent typified by phosphoryl chloride is allowed to act on a compound represented by the formula (5) or a tautomer thereof to prepare a trihalogenated compound (4). An amine ($H_2N$—$R^1$) is then allowed to act on the compound (4) to cyclize it, thereby giving a compound (1) in which $R^2$ is a halogen atom. The halogen-substituted site of this compound is then reduced, thereby giving a compound (1) in which $R^2$ is a hydrogen atom.

Here, the tautomer of the compound (5) includes that having the following structure:

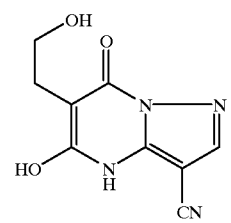

The compound (5) used herein can be prepared in accordance with the following process (b): Process (b):

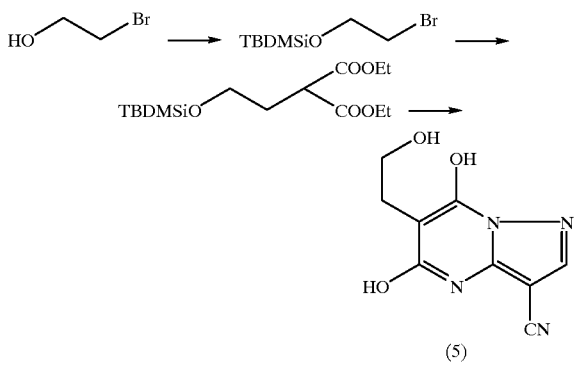

(5)

wherein TBDMSi represents a tert-butyldimethylsilyl group.

More specifically, bromoethanol is tert-butyldimethylsilylated with tert-butyldimethylsilyl chloride, the silylated product is condensed with diethyl malonate in the presence of an alkali such as sodium ethoxide, and the condensate is then allowed to react with 3-amino-4-cyanopyrazole, whereby the compound (5) can be obtained.

Pyrazolopyrimidine derivatives including the compounds of the general formulae (2), (3), (4) and (5), which are represented by the following general formula (6):

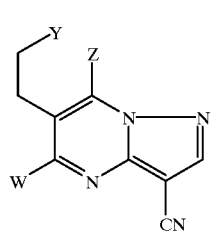

(6)

wherein W represents a hydroxyl group, a halogen atom or an alkoxycarbonyl group, the alkyl moiety of which is a linear, branched or cyclic alkyl group having 1 to 10 carbon atoms, Y represents a hydroxyl group or a halogen atom, and Z represents a hydroxyl group or a halogen atom, or tautomers thereof are important compounds as intermediates useful for preparation of the compounds (1) according to the present invention.

Examples of the compounds represented by the general formula (6) include ethyl 3-cyano-6-(2-hydroxyethyl) pyrazolo[1,5-a]pyrimidin-7(4H)-one-5-carboxylate, ethyl 7-chloro-6-(2-chloroethyl)-3-cyanopyrazolo[1,5-a] pyrimidine-5-carboxylate, 6-(2-chloroethyl)-3-cyano-5,7-dichloropyrazolo[1,5-a]pyrimidine and 3-cyano-5-hydroxy-6-(2-hydroxyethyl)pyrazolo[1,5-a]pyrimidin-7(4H)-one.

The compounds (1) according to the present invention can be prepared by the treatment of a compound (2) or (4) with an amine [$N_2N-R^1$] to cyclize it and the further conversion of the site of $R^2$ in the resultant compound if desired.

The amine is generally used in a proportion of 1.0 to 10.0 mol, preferably 1.0 to 2.5 mol based on the compound (2) or (4). As the catalyst for the reaction, is used a tertiary organic amine or an inorganic base. Specific examples thereof include N,N-diisopropylethylamine, triethylamine, anhydrous potassium carbonate and anhydrous sodium carbonate. These catalysts are generally used in a proportion of 0.5 to 30.0 mol, preferably 2.0 to 5.0 mol based on the compound (2) or (4). $R^1$—$NH_2$, which is a raw amine, may be used in great excess to conduct the reaction without using the catalyst. No particular limitation is imposed on the solvent used in the reaction so far as it is a nonaqueous solvent which can solve the two raw materials therein. Specific examples thereof include N,N-dimethylformamide, chloroform and dichloromethane. Specifically, the amount of the solvent used may be 5 to 100 times as much as the amount of the raw compounds. These solvents may be used either singly or in any combination thereof. The solvent may be selected according to the physical properties of the raw compounds and catalyst used. The reaction temperature in the preparation process of the present invention may be any temperature of from room temperature to a temperature near the boiling point of the solvent. However, room temperature is preferred. The reaction time required for the preparation process of the present invention varies according to various conditions, and is from 30 minutes to 30 days. The treatment and purification after the reaction may be conducted by a suitable combination of ordinary methods, for example, quenching with water, extraction with solvent, column chromatography and recrystallization. By these processes, the compound (1) in which $R^2$ is an alkoxycarbonyl group is obtained from the compound (2), while the compound (1) in which $R^2$ is a halogen atom is obtained from the compound (4).

The compound (1) in which $R^2$ is a carboxyl group is obtained by hydrolyzing the compound in which $R^2$ is an alkoxycarbonyl group. The hydrolysis is carried out by adding the raw material to a mixture of a polar solvent such as tetrahydrofuran or ethanol or a mixed solvent thereof and an aqueous solution of alkali such as sodium hydroxide to conduct a reaction under cooling with ice water or at room temperature to a temperature near the boiling point of the solvent.

The compound (1) in which $R^2$ is an amino group can be prepared by using, as a raw material, the compound in which $R^2$ is a carboxyl group. A halogenated formic ester is first allowed to act on the compound, in which $R^2$ is a carboxyl group, in the presence of a basic catalyst in a solvent such as acetone, chloroform or dichloromethane to prepare a mixed acid anhydride derivative. The reaction solvent is required to be a nonaqueous solvent and have no active group such as a hydroxyl group. It is preferable to use a solvent dried by a method known per se in the art. The basic catalyst is preferably a tertiary amine, with triethylamine being particularly preferred. The halogenated formic ester is preferably ethyl chloroformate or isopropyl chloroformate. In the reaction in which the mixed acid anhydride is prepared, the reaction temperature is preferably a temperature of the order of $-20°$ C. to room temperature. The isolation of the mixed acid anhydride is not conducted, and the reaction mixture is allowed to react with an azide ion as it is. It is preferable to use sodium azide as a source of the azide ion. An aqueous solution of this compound is poured into a solution in which the mixed acid anhydride has been formed, thereby giving an acylazide derivative. The reaction temperature at this time is preferably a temperature of the order of $-20°$ C. to room temperature. The acylazide derivative is isolated by a process such as filtration without purification. The acylazide derivative containing some water is added to a solvent such as toluene, and a rearrangement reaction is accelerated by heating and stirring to complete the conversion into the amino group.

The compound (1) in which $R^2$ is a hydrogen atom can be prepared by using, as a raw material, the compound in which $R^2$ is a halogen atom. The compound in which $R^2$ is a halogen atom is first reduced. It is desired that the site of the halogen atom should be selectively reduced. Specifically, the compound (1) in which $R^2$ is a halogen atom is dissolved in an alcohol such as methanol, or a mixed solvent of an alcohol such as methanol and an inert solvent such as tetrahydrofuran, and proper amounts of palladium chloride and sodium borohydride are then added to conduct a reaction at a temperature under cooling with ice water to room temperature for several minutes to several hours, thereby completing the reduction. The treatment and purification after the reaction may be conducted by a suitable combination of ordinary methods, for example, filtration of by-products, removal of solvent by distillation, column chromatography and recrystallization. By these processes, the compound (1) in which $R^2$ is a hydrogen atom is obtained from the compound in which $R^2$ is a halogen atom.

The compound (2) and the compound (4) are obtained by halogenating the compound (3) and the compound (5), respectively. No particular limitation is imposed on the halogenating reagent used herein. However, an example thereof includes phosphorus oxychloride. The halogenating reagent is generally used in a proportion of 1.0 to 10.0 mol, preferably 2.0 to 5.0 mol based on the compound (3) or the compound (5). No particular limitation is imposed on a solvent used in the reaction so far as it is a nonaqueous solvent. Specific examples thereof include N,N-dimethylformamide, chloroform and dichloromethane. When the halogenating reagent is liquid, the reaction may be conducted without using any solvent. In order to facilitate the progress of the reaction, a basic catalyst may be used. The reaction may also be performed under a nitrogen atmosphere. The reaction temperature varies according to the physical properties of the solvent, halogenating reagent and catalyst used. However, the reaction is preferably conducted while heating under reflux. The treatment and purification after the reaction may be performed in accordance with the ordinary methods. However, it is necessary to take care to prevent the resultant compound from being decomposed in some cases. The dihalogenated compound (2) is obtained from the compound (3), while the trihalogenated compound (4) is obtained from the compound (5).

The compounds (1) or the salts thereof may be used as medicines for respiratory diseases by themselves, but may also be formulated into various preparation forms (compositions) generally used in medicines. Such preparation forms include inhalants, injections, oral preparations, intrarectal preparations and the like.

The medicines of these preparation forms may contain, in addition to the compound (1) or the salt thereof, pharmaceutically acceptable carriers. Examples of such carriers include excipients, binders, coating agents, lubricants, sugar-coatings, disintegrators, extending agents, taste and smell corrigents, emulsifying, solubilizing or dispersing agents, stabilizers, pH adjusters, isotonicity agents and the like.

The preferable dose of the above-described medicine according to the present invention varies according to the condition, sex, age and body dimensions of a patient to be administered, and the like. However, it is preferable to administer the medicine in a dose of generally 1 to 1,000 mg per day for an adult in terms of the compound (1) or the salt thereof. The medicine is preferably administered at once or in several portions a day.

EXAMPLES

The present invention will hereinafter be described in more detail by the following Examples. However, the present invention is not limited in any way to these examples.

Synthesis Example (1)

Preparation of ethyl (tetrahydro-2-oxo-3-furyl)glyoxylate:

Metal sodium in an amount of 25.80 g was added to 500 ml of dried ethanol and dissolved therein. Then, 148.21 g of diethyl oxalate were added, and the reaction system was chilled to −15 to −10° C. A solution of 88.79 g of γ-butyrolactone in 60 ml of ethanol was added dropwise to the mixture while maintaining this temperature, and after the resultant mixture was stirred for 2 hours, it was stirred at room temperature for 16 hours. The reaction mixture was poured into 1 liter of ice water, and the pH of the mixture was then adjusted to 4 to 5 with concentrated hydrochloric acid, and the mixture was extracted with chloroform. The chloroform layer was dried over anhydrous sodium sulfate, and the solvent was distilled off under reduced pressure. The crude product thus obtained was distilled under reduced pressure to give a fraction of 150 to 160° C. (5–6 mmHg) as the intended product. Pale yellow liquid, 156.21 g (yield: 83.1%).

$^1$H-NMR (CDCl$_3$, ppm): 1.39(3H,t,J=7.4 Hz), 3.30(2H,t, J=7.4 Hz), 4.37(2H,q,J=7.4 Hz), 4.50(2H,t,J=7.4 Hz), 10.92 (1H,brs).

Synthesis Example (2)

Preparation of 4-cyano-3-[[[(ethoxycarbonyl)(tetrahydro-2-oxo-3-furyl)]methylene]amino]pyrazole:

In 200 ml of anhydrous ethanol were successively added 20.00 g (0.185 mmol) of 3-amino-4-cyanopyrazole, 37.35 g (0.201 mmol) of ethyl (tetrahydro-2-oxo-3-furyl)glyoxylate and 4.00 g of a boron trifluoride methanol complex, and the mixture was stirred overnight at room temperature. A part of the solvent was distilled off under reduced pressure, and solids deposited were collected by filtration and dried to give 31.32 g (yield: 61.2%) of the intended product.

$^1$H-NMR (DMSO-d$_6$, ppm): 1.15(3H,t,J=7.3 Hz), 2.84 (2H,t,J=7.3 Hz), 4.12(2H,q,J=7.3 Hz), 4.30(2H,t,J=7.3 Hz), 8.46(1H,s), 9.23(1H,s), 13.33(1H,s).

Synthesis Example (3)

Preparation of ethyl 3-cyano-6-(2-hydroxyethyl)pyrazolo[1,5-a]pyrimidin-7(4H)-one-5-carboxylate:

Anhydrous triethylamine in an amount of 200 ml was added to 31.20 g (0.113 mmol) of 4-cyano-3-[[[(ethoxycarbonyl)-(tetrahydro-2-oxo-3-furyl)]methylene] amino]pyrazole, and the mixture was stirred overnight at room temperature. Triethylamine was distilled off under reduced pressure to give 31.20 g (yield: 100%) of the intended product.

$^1$H-NMR (DMSO-d$_6$, ppm): 1.00(3H,t,J=7.3 Hz), 3.03 (2H,t,J=7.6 Hz), 4.17(2H,q,J=7.3 Hz), 4.39(2H,t,J=7.6 Hz), 8.43(1H,s), 9.46(1H,s), 13.26(1H,s).

Synthesis Example (4)

Preparation of ethyl 7-chloro-6-(2-chloroethyl)-3-cyanopyrazolo[1,5-a]pyrimidine-5-carboxylate:

Under a nitrogen atmosphere, 120 ml of phosphorus oxychloride were added to 10.00 g (36.20 mmol) of ethyl 3-cyano-6-(2-hydroxyethyl)pyrazolo[1,5-a]pyrimidin-7 (4H)-one-5-carboxylate, and the mixture was refluxed for 3 hours with stirring. Further, 12 ml of triethylamine were added, and the resultant mixture was heated and stirred for 2 hours. Thereafter, the reaction mixture was concentrated under reduced pressure. The residue was poured into ice water, and solids deposited were collected by filtration, washed with water and dried. The solids were subjected to column chromatography on silica gel (chloroform) to give 7.07 g (yield: 62.4%) of the intended product.

$^1$H-NMR (CDCl$_3$, ppm): 1.50(3H,t,J=7.6 Hz), 3.58(2H,t, J=7.0 Hz), 3.83(2H,t,J=7.0 Hz), 4.52(2H,q,J=7.6 Hz), 8.55 (1H,s).

Synthesis Example (5)

Preparation of ethyl 3-cyano-8-cyclopentyl-6,7-dihydro-8H-pyrrolo[3,2-e]pyrazolo[1,5-a]pyrimidine-5-carboxylate (Compound 11):

While stirring at room temperature, 15.0 ml of cyclopentylamine were added at once to a solution of 10.0 g (31.93 mmol) of ethyl 7-chloro-6-(2-chloroethyl)-3-cyanopyrazolo[1,5-a]pyrimidine-5-carboxylate in 80 ml of anhydrous dimethylformamide. The resultant mixture was then stirred for 5 hours at the same temperature. The reaction mixture was then poured into ice water, and solids deposited were collected by filtration, washed with water and air-dried to give 10.02 g (yield: 96.4%) of the intended product.

$^1$H-NMR (CDC13, ppm): 1.46(3H,t,J=7.3 Hz), 1.60–1.90 (6H,m), 1.90–2.15(2H,m), 3.54(2H,t,J=8.9 Hz), 3.95(2H,t,J=8.9 Hz), 4.44(2H,q,J=7.3 Hz), 5.88–6.05(1H,m), 8.24(1H, s).

Synthesis Example (6)

Preparation of ethyl 3-cyano-8-cyclohexyl-6,7-dihydro-8H-pyrrolo[3,2-e]pyrazolo[1,5-a]pyrimidine-5-carboxylate (Compound 12):

The intended compound was obtained in 96.5% yield in the same manner as in Synthesis Example (5) using ethyl 7-chloro-6-(2-chloroethyl)-3-cyanopyrazolo[1,5-a]-pyrimidine-5-carboxylate and cyclohexylamine.

$^1$H-NMR (CDCl$_3$, ppm): 1.45(3H,t,J=7.3 Hz), 1.35–2.00 (10H,m), 3.52(2H,t,J=8.9 Hz), 3.94(2H,t,J=8.9 Hz), 4.44 (2H,q,J=7.3 Hz), 5.33–5.48(1H,m), 8.24(1H,s).

Synthesis Example (7)

Preparation of ethyl 8-sec-butyl-3-cyano-6,7-dihydro-8H-pyrrolo[3,2-e]pyrazolo[1,5-a]pyrimidine-5-carboxylate (Compound 13):

The intended compound was obtained in 95.6% yield in the same manner as in Synthesis Example (5) using ethyl 7-chloro-6-(2-chloroethyl)-3-cyanopyrazolo[1,5-a]pyrimidine-5-carboxylate and sec-butylamine.

$^1$H-NMR (CDCl$_3$, ppm): 0.93(3H,t,J=7.3 Hz), 1.34(3H, d,J=6.8 Hz), 1.46(3H,t,J=7.0Hz), 1.58–1.85(2H,m), 3.54 (2H,t,J=6.8 Hz), 3.76–4.00(2H,m), 4.45(2H,q,J=7.0 Hz), 5.60–5.85(1H,m), 8.24(1H,s).

Synthesis Example (8)

Preparation of ethyl 8-tert-butyl-3-cyano-6,7-dihydro-8H-pyrrolo[3,2-e]pyrazolo[1,5-a]pyrimidine-5-carboxylate (Compound 18):

The intended compound was obtained in the same manner as in Synthesis Example (5) using ethyl 7-chloro-6-(2-chloroethyl)-3-cyanopyrazolo[1,5-a]pyrimidine-5-carboxylate and tert-butylamine.

$^1$H-NMR (CDCl$_3$, ppm): 1.45(3H,t,J=7.2 Hz), 1.74(9H,s), 3.45(2H,t,J=8.9 Hz), 4.12(2H,t,J=8.9 Hz), 4.44(2H,q,J=7.2 Hz), 8.28(1H,s).

Synthesis Example (9)

Preparation of 3-cyano-8-cyclopentyl-6,7-dihydro-8H-pyrrolo[3,2-e]pyrazolo[1,5-a]pyrimidine-5-carboxylic acid (Compound 8):

To 10.00 g (30.73 mmol) of ethyl 3-cyano-8-cyclopentyl-6,7-dihydro-8H-pyrrolo[3,2-e]pyrazolo[1,5-a]pyrimidine-5-carboxylate were added 200 ml of tetrahydrofuran and. 200 ml of ethanol. While stirring under cooling with ice water, 54 ml of a 1N aqueous solution of sodium hydroxide were added to the mixture, and stirring was continued for 1 hour at the same temperature. Furthermore, 500 ml of a 1:1 mixed solvent of tetrahydrofuran and ethanol were added, and the resultant mixture was stirred at the same temperature for a while. The reaction mixture was then acidified with concentrated hydrochloric acid, and insoluble solids were collected by filtration, washed with water and dried to give 9.09 g (yield: 91.04%) of the intended compound.

$^1$H-NMR (DMSO-d$_6$, ppm): 1.50–2.00(8H,m), 3.83(2H, t,J=8.4 Hz), 3.95(2H,t,J=8.4 Hz), 5.70–5.95(1H,m), 8.67 (1H,s), 13.13(1H,brs).

Synthesis Example (10)

Preparation of 3-cyano-8-cyclohexyl-6,7-dihydro-8H-pyrrolo[3,2-e]pyrazolo[1,5-a]pyrimidine-5-carboxylic acid (Compound 9):

The intended compound was obtained in the same manner as in Synthesis Example (9) except that ethyl 3-cyano-8-cyclohexyl-6,7-dihydro-8H-pyrrolo[3,2-e]pyrazolo[1,5-a] pyrimidine-5-carboxylate was used. (yield: quantitative)

$^1$H-NMR (CD$_3$OD, ppm): 1.30–2.15(10H,m), 3.58(2H,t, J=8.9 Hz), 4.14(2H,t,J=8.9 Hz), 5.50–5.68(1H,m), 8.52(1H, s).

Synthesis Example (11)

Preparation of 8-sec-butyl-3-cyano-6,7-dihydro-8H-pyrrolo[3,2-e]pyrazolo[1,5-a]pyrimidine-5-carboxylic acid (Compound 10):

The intended compound was obtained in 92.8% yield in the same manner as in Synthesis Example (9) except that ethyl 8-sec-butyl-3-cyano-6,7-dihydro-8H-pyrrolo[3,2-e] pyrazolo[1,5-a]pyrimidine-5-carboxylate was used.

$^1$H-NMR (DMSO-d$_6$, ppm): 0.85(3H,t,J=7.2 Hz), 1.27 (3H,d,J=6.8 Hz), 1.45–1.80(2H,m), 3.41(2H,t,J=8.6 Hz), 3.75–4.00(2H,m), 5.45–5.70(1H,m), 8.67(1H,s), 13.49(1H, brs).

Synthesis Example (12)

Preparation of 8-tert-butyl-3-cyano-6,7-dihydro-8H-pyrrolo [3,2-e]pyrazolo[1,5-a]pyrimidine-5-carboxylic acid (Compound 17):

The intended compound was obtained in the same manner as in Synthesis Example (9) except that ethyl 8-tert-butyl-3-cyano-6,7-dihydro-8H-pyrrolo[3,2-e]pyrazolo[1,5-a] pyrimidine-5-carboxylate was used.

$^1$H-NMR (DMSO-d$_6$, ppm): 1.68(9H,s), 3.30(2H,t,J=8.8 Hz), 4.15(2H,t,J=8.8 Hz), 8.69(1H,s), 13.49(1H,brs).

Synthesis Example (13)

Preparation of 5-amino-3-cyano-8-cyclopentyl-6,7-dihydro-8H-pyrrolo[3,2-e]pyrazolo[1,5-a]pyrimidine (Compound 5):

To 3.00 g (10.09 mmol) of 3-cyano-8-cyclopentyl-6,7-dihydro-8H-pyrrolo[3,2-e]pyrazolo[1,5-a]pyrimidine-5-carboxylic acid were added 40 ml of anhydrous acetone and 1.8 ml (d=0.726, 12.94 mmol) of triethylamine. While stirring under cooling with ice water, a solution of 1.20 ml (d=1.135, 12.55 mmol) of ethyl chloroformate in 5 ml of anhydrous acetone was added to the mixture, and the mixture was stirred for 30 minutes at the same temperature. Furthermore, a solution of 1.40 g (21.54 mmol) of sodium azide in 2.5 ml of water was added while stirring at the same temperature, and the resultant mixture was stirred for 30 minutes at the same temperature. The reaction mixture was poured into ice water, and insoluble solids were collected by filtration and washed with water. The insoluble solids were added to 100 ml of toluene, and after the mixture was refluxed for 1 hour with stirring, toluene was distilled off under reduced pressure. The residue was dissolved in chloroform, and hexane was added to the solution. Solids deposited were collected by filtration and dried to give 1.50 g (yield: 60.0%) of the intended compound.

m.p.: 265° C. IR (KBr tablet, cm$^{-1}$): 3500, 3300, 3260, 3136, 2208, 1647, 1613, 1574, 1528, 1417, 1290, 1246, 1218, 741. $^1$H-NMR (CDCl$_3$, ppm): 1.55–2.10(8H,m), 2.95 (2H,t,J=8.9 Hz), 3.81(2H,t,J=8.9 Hz), 5.60–5.80(1H,m), 5.86(2H,brs), 7.94(1H,s).

Synthesis Example (14)

Preparation of 5-amino-3-cyano-8-cyclohexyl-6,7-dihydro-8H-pyrrolo[3,2-e]pyrazolo[1,5-a]pyrimidine (Compound 6):

The intended compound was obtained in 41.7% yield in the same manner as in Synthesis Example (13) except that 3-cyano-8-cyclohexyl-6,7-dihydro-8H-pyrrolo[3,2-e]pyrazolo[1,5-a]pyrimidine-5-carboxylic acid was used.

m.p.: 253–255° C. IR (KBr tablet, cm$^{-1}$): 3480, 3300, 3147, 2214, 1646, 1613, 1570, 1530, 1410, 1291, 1238. $^1$H-NMR (CDCl$_3$, ppm): 1.00–1.95(10H,m), 2.93(2H,t,J=9.2 Hz), 3.81(2H,t,J=9.2 Hz), 5.05–5.18(1H,m), 5.38(2H, brs), 7.95(1H,s).

Synthesis Example (15)

Preparation of 5-amino-8-sec-butyl-3-cyano-6,7-dihydro-8H-pyrrolo[3,2-e]pyrazolo[1,5-a]pyrimidine (Compound 7):

The intended compound was obtained in 51.9% yield in the same manner as in Synthesis Example (13) except that 8-sec-butyl-3-cyano-6,7-dihydro-8H-pyrrolo[3,2-e]pyrazolo[1,5-a]pyrimidine-5-carboxylic acid was used.

m.p.: 191–192° C. IR (KBr tablet, cm$^{-1}$): 3480, 3320, 3140, 2211, 1655, 1616, 1577, 1529. $^1$H-NMR (CDCl$_3$, ppm): 0.91(3H,t,J=7.3 Hz), 1.23(3H,d,J=7.0 Hz), 1.45–1.75 (2H,m), 2.96(2H,t,J=9.3 Hz), 3.65–3.86(2H,m), 5.30–5.50 (1H,m), 5.78(2H,brs), 7.94(1H,s).

Synthesis Example (16)

Preparation of 5-amino-8-tert-butyl-3-cyano-6,7-dihydro-8H-pyrrolo[3,2-e]pyrazolo[1,5-a]pyrimidine (Compound 16):

The intended compound was obtained in 36.2% yield in the same manner as in Synthesis Example (13) except that 8-tert-butyl-3-cyano-6,7-dihydro-8H-pyrrolo[3,2-e]pyrazolo[1,5-a]pyrimidine-5-carboxylic acid was used.

m.p.: 229.5–232.0° C. IR (KBr tablet, cm$^{-1}$): 3480, 3320, 3140, 2216, 1653, 1611, 1566, 1513, 1228, 1213. $^1$H-NMR (CDCl$_3$, ppm): 1.66(9H,s), 2.82(2H,t,J=8.9 Hz), 3.98(2H,t, J=8.9 Hz), 5.23(2H,brs), 7.96(1H,s).

Synthesis Example (17)

Preparation of 1-bromo-2-tert-butyldimethylsilyloxyethane:

To 40 ml of acetonitrile dried over molecular sieves were added 3.50 g of tert-butyldimethylsilyl chloride and 4.00 g of imidazole. The mixture was stirred for 10 minutes at room temperature. To the mixture were added 2.64 g of 2-bromoethanol, and the resultant mixture was stirred for additional 6 hours at room temperature. The solvent was distilled off under reduced pressure, and ethyl acetate was added to the residue. After the ethyl acetate layer was washed with a saturated aqueous solution of sodium hydrogencarbonate and dried over anhydrous sodium sulfate, the solvent was distilled off under reduced pressure. The thus-obtained crude product was subjected to column chromatography on silica gel (hexane:ethyl acetate=2:1) to give 4.40 g (yield: 87.0%) of the intended product. Colorless liquid.

$^1$H-NMR (CDl$_3$, ppm): −0.10(6H,s), 0.82(9H,s), 3.31(2H, t,J=6.3 Hz), 3.80(2H,t,J=6.3 Hz).

Synthesis Example (18)

Preparation of diethyl 2-(2-tert-butyldimethylsilyloxyethyl) malonate:

In 1.70 liters of ethanol dried over molecular sieves were dissolved 22.90 g of metal sodium. To the solution were added 131.0 g of diethyl malonate and 230 g of 1-bromo-2-tert-butyldimethylsilyloxyethane. The mixture was stirred overnight while heating under reflux. After most of the solvent was distilled off under reduced pressure, a small amount of ether was added. Crystals deposited were separated by filtration, and the filtrate was concentrated and subjected to column chromatography on silica gel (hexane, hexane:ethyl acetate=10:1) to give 234.42 g (yield: 89.9%) of the intended product. Colorless liquid.

$^1$H-NMR (CDCl$_3$, ppm): 0.02(6H,s), 0.87(9H,s), 1.25 (6H,t,J=7.2 Hz), 2.10(2H,q,J=6.5 Hz), 3.54–3.66(3H,m), 4.17(4H,m).

Synthesis Example (19)

Preparation of 3-cyano-5-hydroxy-6-(2-hydroxyethyl) pyrazolo[1,5-a]pyrimidin-7(4H)-one:

After 4.14 g of metal sodium were dissolved in 500 ml of ethanol dried over molecular sieves, 37.50 g of diethyl 2-(2-tert-butyldimethylsilyloxyethyl)malonate and 9.72 g of 3-amino-4-cyanopyrazole were added to the solution. The mixture was stirred for 4 days while heating under reflux. Most of the solvent was distilled off under reduced pressure, and ether was added to the residue. Crystals deposited were collected by filtration, dried and then dissolved in 700 ml of methanol. To the solution were added 12.0 ml of concentrated hydrochloric acid, and the mixture was stirred for a while. Sodium chloride deposited was separated by filtration, and the filtrate was concentrated under reduced pressure. Ether was added again, and crystals deposited were collected by filtration and dried. Amount produced: 17.60 g. Yield: 88.8%. Pale brown crystals.

$^1$H-NMR (DMSO-d$_6$, ppm): 2.66(2H,t,J=6.5 Hz), 3.52 (2H,t,J=6.5 Hz), 8.22(1H,s).

Synthesis Example (20)

Preparation of 6-(2-chloroethyl)-3-cyano-5,7-dichloropyrazolo[1,5-a]pyrimidine:

To 16.40 g of 3-cyano-.5-hydroxy-6-(2-hydroxyethyl) pyrazolo[1,5-a]pyrimidin-7(4H)-one were added 100 ml of phosphorus oxychloride and 13.58 g of triethylamine. The mixture was stirred for 2 hours while heating under reflux. Since spots attributable to the raw materials on TLC disappeared, the stirring was stopped. After excess phosphorus oxychloride was distilled off under reduced pressure, the residue was poured into ice water and extracted with chloroform. The chloroform layer was dried over anhydrous sodium sulfate, and the solvent was distilled off under reduced pressure. The crude product thus obtained was subjected to column chromatography on silica gel (chloroform:methanol=10:1) to give 9.03 g (yield: 44.0%) of the intended product. White crystals.

$^1$H-NMR (CDCl$_3$, ppm): 3.51(2H,t,J=7.0 Hz), 3.85(2H,t, J=7.0 Hz), 8.46(1H,s).

Synthesis Example (21)

Preparation of 8-tert-butyl-5-chloro-3-cyano-6,7-dihydro-8H-pyrrolo[3,2-e]pyrazolo[1,5-a]pyrimidine (Compound 15):

In 30 ml of dimethylformamide were dissolved 2.50 g of 6-(2-chloroethyl)-3-cyano-5,7-dichloropyrazolo[1,5-a] pyrimidine, and 900 mg of tert-butylamine and 2.00 g of triethylamine were added to the solution. The mixture was stirred for 4 hours at room temperature. Excess amines and the solvent were distilled off under reduced pressure, and the residue was dissolved in chloroform. After the chloroform layer was washed with saturated brine and then dried over anhydrous sodium sulfate, the solvent was distilled off. The residue was treated with a chloroform-ether system to deposit crystals. The crystals were collected by filtration and dissolved in 120 ml of ethanol under heating to conduct recrystallization. Amount produced: 2.04 g. Yield: 81.6%. Pale brown crystals.

m.p.: 245° C. (decomposed). IR (KBr tablet, cm$^{-1}$): 2200, 1600, 1580, 1500. $^1$H-NMR (CDCl$_3$, ppm): 1.79(9H,s), 3.16(2H,t,J=9.2 Hz), 4.13(2H,t,J=9.2 Hz), 8.17(1H,s).

Synthesis Example (22)

Preparation of 5-chloro-3-cyano-8-cyclopentyl-6,7-dihydro-8H-pyrrolo[3,2-e]pyrazolo[1,5-a]pyrimidine (Compound 3):

The intended compound was obtained in an amount of 2.26 g (yield: 83.1%) in the same manner as in Synthesis Example (21) except that 2.60 g of 6-(2-chloroethyl)-3-cyano-5,7-dichloropyrazolo[1,5-a]pyrimidine were allowed to react with 940 mg of cyclopentylamine and 2.0 g of triethylamine. Pale brown crystals.

m.p.: 208° C. IR (KBr tablet, cm$^{-1}$): 2200, 1630, 1610, 1500. $^1$H-NMR (CDCl$_3$, ppm): 1.74(6H,m), 1.98(2H,m), 3.20(2H,t,J=9.2 Hz), 3.93(2H,t,J=9.2 Hz), 5.82(1H,m), 8.14 (1H,s).

Synthesis Example (23)

Preparation of 8-sec-butyl-5-chloro-3-cyano-6,7-dihydro-8H-pyrrolo[3,2-e]pyrazolo[1,5-a]pyrimidine (Compound 4):

The intended compound was obtained in an amount of 2.12 g (yield: 84.8%) in the same manner as in Synthesis Example (21) except that 2.50 g of 6-(2-chloroethyl)-3-cyano-5,7-dichloropyrazolo[1,5-a]pyrimidine were allowed to react with 900 mg of sec-butylamine and 2.00 g of triethylamine. Pale brown crystals.

m.p.: 227° C. IR (KBr tablet, cm$^{-1}$): 2220, 1620, 1600, 1500, 1300. $^1$H-NMR (CDCl$_3$, ppm): 0.93(3H,t,J=7.3 Hz), 1.30(3H,d,J=7.0 Hz), 1.70(2H,m), 3.20(2H,t,J=9.5 Hz), 3.85 (2H,m), 3.57(1H,m), 8.15(1H,s).

Synthesis Example (24)

Preparation of 8-tert-butyl-3-cyano-6,7-dihydro-8H-pyrrolo[3,2-e]pyrazolo[1,5-a]pyrimidine (Compound 14):

In a mixed solvent of 160 ml of tetrahydrofuran and 80 ml of methanol were dissolved 4.00 g of 8-tert-butyl-5-chloro-3-cyano-6,7-dihydro-8H-pyrrolo[3,2-e]pyrazolo[1,5-a] pyrimidine at 40° C., and the reaction system was then cooled to 0° C. To the solution were gradually added 1.28 g of palladium chloride and 2.75 g of sodium borohydride, and the mixture was stirred for 30 minutes at 0° C. Furthermore, 2.56 g of palladium chloride and 5.49 g of sodium borohydride were gradually added, and the resultant mixture was stirred for 30 minutes at 0° C. and for 1 hour at room temperature. Solids were removed by filtration, and most of the filtrate was evaporated under reduced pressure. The resultant crude product was subjected to column chromatography on silica gel (chloroform:methanol=10:1) to give 1.70 g (yield: 54.3%) of the intended product. Recrystallization was conducted from ethanol. White crystals.

m.p.: 201–202° C. IR (KBr tablet, cm$^{-1}$): 2220, 1610, 1590, 1500. $^1$H-NMR (CDCl$_3$, ppm): 1.72(9H,s), 3.11(2H, t,J=9.2 Hz), 4.06(2H,t,J=9.2 Hz), 8.03(1H,s), 8.17(1H,s).

Synthesis Example (25)

Preparation of 3-cyano-8-cyclopentyl-6,7-dihydro-8H-pyrrolo[3,2-e]pyrazolo[1,5-a]pyrimidine (Compound 1):

Synthesis was conducted in the same manner as in Synthesis Example (24) except that 2.85 g of 5-chloro-3-cyano-8-cyclopentyl-6,7-dihydro-8H-pyrrolo[3,2-e]pyrazolo[1,5-a]pyrimidine were used. The resultant crude product was subjected to column chromatography on silica gel (ethyl acetate) to give 660 mg (yield: 26.4%) of the intended product. Recrystallization was conducted from ethanol. Pale brown crystals.

m.p. : 124–125° C. IR (KBr tablet, cm$^{-1}$): 2220, 1620, 1610, 1500, 1290. $^1$H-NMR (CDCl$_3$, ppm): 1.73(6H,m), 1.97(2H,m), 3.22(2H,t,J=9.2 Hz), 3.90(2H,t,J=9.2 Hz), 5.86 (1H,m), 8.02(1H,s), 8.17(1H,s).

Synthesis Example (26)

Preparation of 8-sec-butyl-3-cyano-6,7-dihydro-8H-pyrrolo[3,2-e]pyrazolo[1,5-a]pyrimidine (Compound 2):

Synthesis was conducted in the same manner as in Synthesis Example (24) except that 4.308 g of 8-sec-butyl-5-chloro-3-cyano-6,7-dihydro-8H-pyrrolo[3,2-e]pyrazolo[1, 5-a]pyrimidine were used. The resultant crude product was subjected to column chromatography on silica gel (ethyl acetate) to give 1.28 g (yield: 34.0%) of the intended product. Recrystallization was conducted from ethanol. Pale gray crystals.

m.p.: 171–172° C. IR (KBr tablet, cm$^{-1}$): 2220, 1620, 1610, 1510, 1280. $^1$H-NMR (CDCl$_3$, ppm): 0.93(3H,t,J=7.3 Hz), 1.31(3H,d,J=7.0 Hz), 1.72(2H,m), 3.26(2H,t,J=9.2 Hz), 3.90(2H,m), 5.60(1H,m), 8.04(1H,s), 8.17(1H,s).

Test Example 1

Tracheodilative effect (in vitro):

With respect to Compound 2, Compound 5, Compound 6, Compound 7 and Compound 16, the tracheodilative effect useful in treatment and/or prevention of respiratory diseases such as asthma was investigated by the Magnus method. A male Hartley albino guinea pig (250 to 300 g) was blow on the head and exsanguinated to death to enucleate its trachea. Strip specimens were prepared from the trachea. Each of the specimens was suspended in a Magnus tube filled with a Krebs-Henseleit solution kept at 37° C. with supply of a mixed gas (95% $O_2$, 5% $CO_2$). A static tension of 1.0 g was loaded to record an isometric tension. Each of test compounds was cumulatively administered to the specimens separately contracted with $1\times10^{-6}$ M carbachol and $3\times10^{-6}$ M histamine to investigate its relaxing effect. After the cumulative administration, $10^{-4}$ M isoproterenol was administered to identify the maximum relaxing effect on the trachea specimen. The maximum relaxation was regarded as 100%, and a negative logarithmic value of the concentration of the test compound, at which the specimen was relaxed by 50%, was calculated out, thereby regarding it as a $pIC_{50}$ value. The results are shown in Table 1. The test revealed that all the compounds according to the present invention have a pharmacological effect higher than a control medicine.

TABLE 1

| | $pIC_{50}$ value | |
| --- | --- | --- |
| | Carbachol | Histamine |
| Compound 2 | 4.72 | 5.20 |
| Compound 5 | 4.73 | 4.90 |
| Compound 6 | 4.65 | 4.79 |
| Compound 7 | 4.74 | 4.81 |
| Compound 16 | 4.63 | 4.79 |
| Theophylline | 2.53 | 3.01 |

Test Example 2
Tracheodilative effect (in vitro):

The $pIC_{50}$ values of the compounds according to the present invention on contraction by $LTD_4$ (concentration: $3\times10^{-8}$ M) were determined by using the enucleated trachea in accordance with the Magnus method in the same manner as in Test Example 1. The results are shown in Table 2. It turns out that the compounds according to the present invention are effective on the contraction by this agent.

TABLE 2

| | $pIC_{50}$ value |
|---|---|
| | $LTD_4$ |
| Compound 5 | 5.39 |
| Compound 6 | 4.95 |
| Compound 7 | 5.43 |
| Theophylline | 3.95 |

Test Example 3
Inhibitory effect on airway-constriction reaction (in vivo):

A group of 6 male Hartley albino guinea pigs (250 to 350 g) was anesthetized with pentobarbital, and the tracheae, esophagi, carotid arteries and jugular veins thereof were cannulated. The experiment was performed by connecting the tracheotomic cannula to a respirator incorporated into a circuit of a bronchospasm transducer (modified Konzet-Lössler method), arresting the spontaneous respiration of each guinea pig with choline chloride succinate (1 mg/kg i.v.) and then practicing artificial ventilation, and an airway-constriction reaction was determined by using an overflow rate of ventilation as an index. Acetylcholine (20 μg/kg) or histamine (20 μg/kg) was intravenously administered upon elapsed time of 15, 30, 60 and 120 minutes after a test compound (100 mg/2 ml/kg) suspended in 1% CMC was administered through the esophageal cannula, thereby observing the airway-constriction reaction elicited. For the sake of comparison, theophylline (100 mg/2 ml/kg) commonly and widely used in the treatment for asthma was used. The inhibitory effect on the airway-constriction reaction was expressed by a value calculated as an inhibitory rate (%). The results are shown in Table 3. It turns out that all the compounds according to the present invention have an excellent inhibitory effect on airway constriction.

TABLE 3

| | Inhibitory rate (%) | |
|---|---|---|
| | Acetylcholine | Histamine |
| Compound 1 | 33.4 | 22.2 |
| Compound 2 | 50.0 | 52.2 |
| Compound 3 | 22.8 | 7.7 |
| Compound 4 | 33.2 | 24.7 |
| Compound 5 | 32.1 | 52.9 |
| Compound 7 | 36.5 | 49.8 |
| Compound 14 | 40.4 | 8.7 |
| Compound 15 | 36.5 | 25.8 |
| Theophylline | 39.5 | 37.7 |

INDUSTRIAL APPLICABILITY

The compounds (1) according to the present invention or salts thereof have excellent tracheobronchodilative effect and inhibitory effect on airway constriction, and are hence useful as medicines having prophylactic and therapeutic effects on respiratory diseases, particularly, bronchial asthma.

What is claimed is:

1. A pyrrolopyrazolopyrimidine derivative represented by the formula (1A):

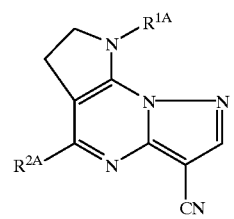

(1A)

wherein $R^{1A}$ represents a linear, branched or cyclic alkyl group having 1 to 10 carbon atoms; and $R^{2A}$ represents a halogen atom, a substituted alkyl group, an amino group which may be substituted, a carboxyl group, an alkoxycarbonyl group, a carbamoyl group, or an alkylcarbamoyl group, or a salt thereof; wherein said substituted alkyl is selected from the group consisting of alkoxyalkyl, aryloxyalkyl, aralkyloxyalkyl, mono-alkyl-aminoalkyl, di-alkyl-aminoalkyl, cyclic aminoalkyl, and hydroxyalkyl; and wherein said substituted amino is selected from the group consisting of mono-dialkylamino, di-alkyl-amino, cyclic amino, alkuylsulfonylamino optionally substituted with halogen, arylsulfonylamino, alkylcarbonylamino, arylcarbonylamino, ureido, substituted ureido, thioureido, substituted thioreido, hydrazino, and substituted hydrazino; and wherein $R^{1A}$ is not a tert-butyl group.

2. The pyrrolopyrazolopyrimidine derivative or the salt thereof according to claim 1, wherein $R^{2A}$ is an amino group or a halogen atom.

3. The pyrrolopyrazolopyrimidine derivative or the salt thereof according to claim 1, wherein $R^{1A}$ is selected from the group consisting of isopropyl, cyclopropyl, sec-butyl, cyclobutyl, 1-ethyl-propyl, tert-amyl, cyclopentyl and cyclohexyl.

4. A pharmaceutical composition comprising the pyrrolopyrazolopyrimidine derivative of claim 1 and a pharmaceutically acceptable carrier.

5. A method for providing bronchodilation to a patient in need thereof comprising administering to said patient an effective amount of the pyrrolopyrazolopyrimidine derivative of claim 1.

6. A method for the treatment of airway constriction and/or bronchial asthma, which comprises the administration of an effective amount of pyrrolopyrazolopyrimidine derivative represented by the formula (1):

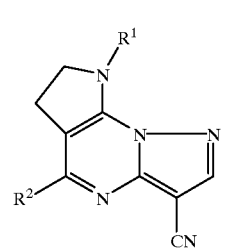

(1)

wherein $R^1$ represents a linear, branched or cyclic alkyl group having 1 to 10 carbon atoms; and $R^2$ represents a hydrogen or halogen atom, a substituted alkyl group, an amino group which may be substituted, a carboxyl group, an alkoxycarbonyl group, a carbamoyl group, or an alkylcarbamoyl group, or a salt thereof to a patient, wherein said substituted alkyl is selected from the group consisting of alkoxyalkyl, aryloxyalkyl, aralkyloxyalkyl, mono-alkyl-aminoalkyl, di-alkyl-aminoalkyl, cyclic aminoalkyl, and hydroxyalkyl; and wherein said substituted amino is selected from the group consisting of mono-dialkylamino, di-alkyl-amino, cyclic amino, alkuylsulfonylamino optionally substituted with halogen, arylsulfonylamino, alkylcarbonylamino, arylcarbonylamino, ureido, substituted ureido, thioureido, substituted thioreido, hydrazino, and substituted hydrazino.

7. The method according to claim 6, wherein $R^1$ is selected from the group consisting of an isopropyl, cyclopropyl, sec-butyl, tert-butyl, cyclobutyl, 1-ethylpropyl, tert-amyl, cyclopentyl, and cyclohexyl group.

8. The method according to claim 6 or 7, wherein $R^2$ is selected from the group consisting of an amino group, a halogen atom, and a hydrogen atom.

* * * * *

UNITED STATES PATENT AND TRADEMARK OFFICE
CERTIFICATE OF CORRECTION

PATENT NO.     : 6,329,382 B1
DATED          : December 11, 2001
INVENTOR(S)    : Namiki et al.

It is certified that error appears in the above-identified patent and that said Letters Patent is hereby corrected as shown below:

Title page,
Item [30], Foreign Application Priority Data should read:
-- [30]           Foreign Application Priority Data
Feb. 14, 1997    (JP) ........................................ 9-047197
Feb. 14, 1997    (JP) ........................................ 9-047211 --

Signed and Sealed this

Twenty-fourth Day of December, 2002

JAMES E. ROGAN
*Director of the United States Patent and Trademark Office*